US012696407B2

(12) United States Patent
Mills et al.

(10) Patent No.: US 12,696,407 B2
(45) Date of Patent: Jul. 28, 2026

(54) ENVIRONMENTAL SENSOR ASSEMBLY

(71) Applicant: ECOSYSTEM INFORMATICS INC.,
Mississauga (CA)

(72) Inventors: Leslie Mills, Mississauga (CA);
Shirook Ali, Mississauga (CA)

(73) Assignee: ECOSYSTEM INFORMATICS INC.,
Mississauga (CA)

( * ) Notice: Subject to any disclaimer, the term of this
patent is extended or adjusted under 35
U.S.C. 154(b) by 173 days.

(21) Appl. No.: 18/620,722

(22) Filed: Mar. 28, 2024

(65) Prior Publication Data
US 2025/0311131 A1      Oct. 2, 2025

(51) Int. Cl.
*G01D 11/24*       (2006.01)
*G01N 33/00*       (2006.01)
*H05K 5/02*        (2006.01)
*H05K 5/06*        (2006.01)

(52) U.S. Cl.
CPC ........... *H05K 5/069* (2013.01); *G01D 11/245*
(2013.01); *G01N 33/0031* (2013.01); *H05K*
*5/0215* (2022.08); *H05K 5/0247* (2013.01)

(58) Field of Classification Search
None
See application file for complete search history.

(56) References Cited

U.S. PATENT DOCUMENTS

| | | | | |
|---|---|---|---|---|
| 6,838,852 B1* | 1/2005 | Namuduri | .......... | G05B 19/0423 |
| | | | | 318/434 |
| 2007/0263367 A1* | 11/2007 | Fischer | ................. | G01D 21/02 |
| | | | | 361/752 |
| 2012/0266671 A1* | 10/2012 | Moser | ................. | G01D 11/245 |
| | | | | 73/431 |
| 2013/0007316 A1* | 1/2013 | Moon | ................. | G05B 19/042 |
| | | | | 710/62 |
| 2013/0321148 A1* | 12/2013 | Daga | ................. | G01N 33/0009 |
| | | | | 340/539.22 |
| 2015/0007636 A1* | 1/2015 | Benkert | ............. | G01N 33/0073 |
| | | | | 73/53.01 |
| 2019/0086282 A1* | 3/2019 | Na | ........................ | G01L 19/147 |
| 2019/0170717 A1* | 6/2019 | Mou | ................. | G01N 33/0031 |
| 2019/0242688 A1* | 8/2019 | Huang | ............... | H05K 7/20172 |
| 2019/0302072 A1* | 10/2019 | Mou | .................... | G01N 33/004 |
| 2020/0105429 A1* | 4/2020 | Roberts | ................. | G01L 19/142 |
| 2020/0132644 A1* | 4/2020 | Micalizzi | ................. | H04Q 9/00 |
| 2021/0003543 A1* | 1/2021 | Hattori | ................. | G01N 29/022 |
| 2022/0128502 A1* | 4/2022 | Vanhelmont | ....... | G01N 33/0031 |

* cited by examiner

*Primary Examiner* — Xanthia C Relford

(57) ABSTRACT

An environmental sensor assembly includes a housing having at least one internal divider defining a sensor compartment and a systems compartment, wherein the sensor compartment defines at least one opening to provide gas communication to the atmosphere; an interconnect providing electrical connections between the sensor compartment and the systems compartment; and a plurality of sensors each mounted in the sensor compartment in a detachable manner and operably connected to the interconnect. The sensor compartment and the systems compartment are sealed and separate.

8 Claims, 4 Drawing Sheets

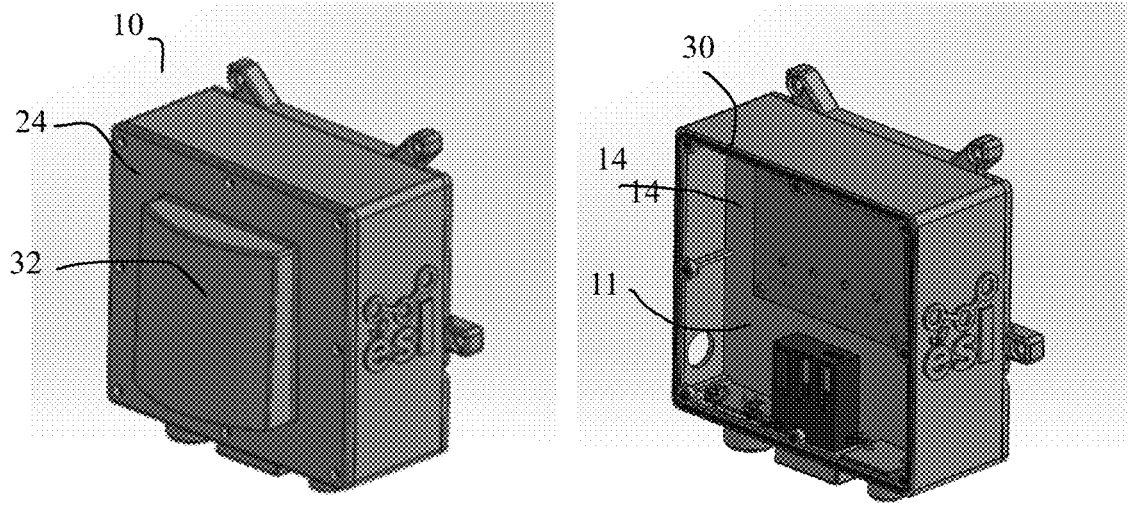
FIG. 2A                    FIG. 2B
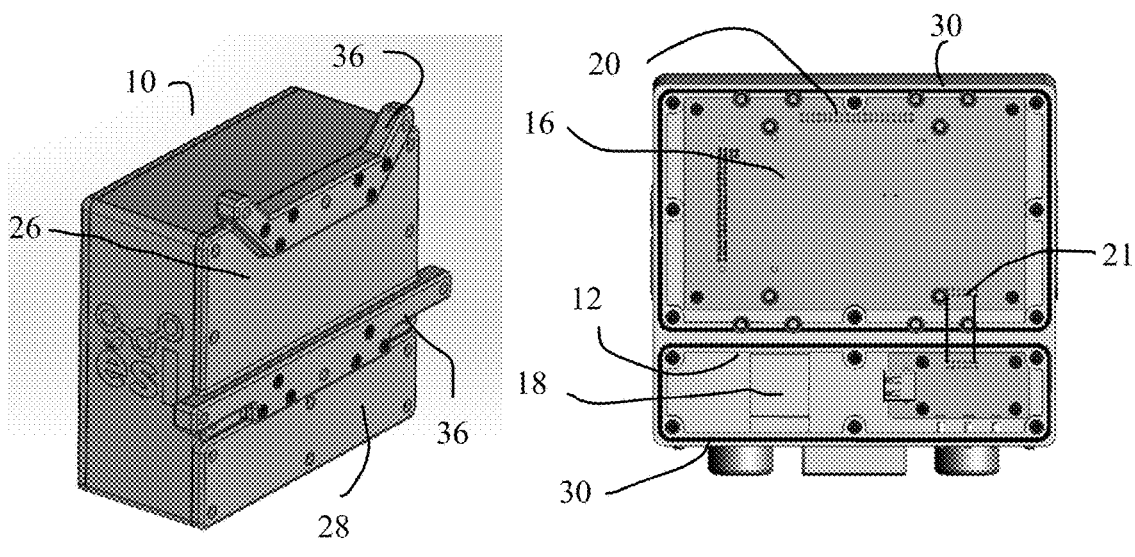
FIG. 2C                    FIG. 2D

C4

ENVIRONMENTAL SENSOR ASSEMBLY

FIELD OF THE INVENTION

The present invention generally relates to a sensor assembly for monitoring environmental conditions, for both stationary and mobile applications.

BACKGROUND

Ambient air parameters, such as the concentration of gaseous air pollutants and air temperature, may be monitored for a variety of reasons, such as alerting populations of health risks, evaluating compliance with air quality standards, and mapping air quality patterns.

Sensors may be stationary or mobile, however, a sensor mounted on a moving vehicle could monitor air quality over a greater geographic area than would be possible if the sensor were stationary. However, changing vehicle motion results in temperature, wind direction, and wind speed variations, which can affect the accuracy of the sensor readings.

Different sensors may be used to monitor different ambient parameters. However, increasing the number of different sensors increases the complexity of a monitoring system, and the amount of the sensor data that needs to be transmitted. This has practical implications for cost, efficiency, and reliability when monitoring is performed on a large scale.

SUMMARY OF THE INVENTION

Embodiments of the present invention relate to a sensor assembly for monitoring environmental conditions. In one aspect, disclosed is an environmental sensor assembly comprising:

(a) a housing having at least one internal divider defining a sensor compartment and a systems compartment, wherein the sensor compartment defines at least one opening to provide gas communication to the atmosphere;

(b) an interconnect providing electrical connections between the sensor compartment and the systems compartment; and (c) a plurality of sensors each mounted in the sensor compartment in a detachable manner and operably connected to the interconnect.

In a preferred embodiment, the systems compartment comprises a second internal divider which defines a controller compartment and a communications compartment, with an interconnect providing electrical connections between the two.

In a preferred embodiment, the sensor compartment includes at least one subchamber separated from the sensor compartment by a baffle or air permeable element which calms air turbulence in the at least one subchamber.

In a preferred embodiment, the sensor compartment comprises a plurality of sensor modules having different "plug and play" connectors.

In some embodiments, the sensor assembly may comprise any combination of features or elements described below or shown in the drawings attached.

BRIEF DESCRIPTION OF THE FIGURES

The accompanying drawings, which are incorporated herein and form a part of the specification, illustrate some, but not the only or exclusive, examples of embodiments and/or features.

FIGS. 2A and 2B shows a front perspective view of one embodiment of a sensor assembly, with and without the front cover. FIG. 2C a rear perspective view of the same embodiment with the rear covers. FIG. 2D shows a rear plan view with the rear cover removed.

DETAILED DESCRIPTION

Figure 1:
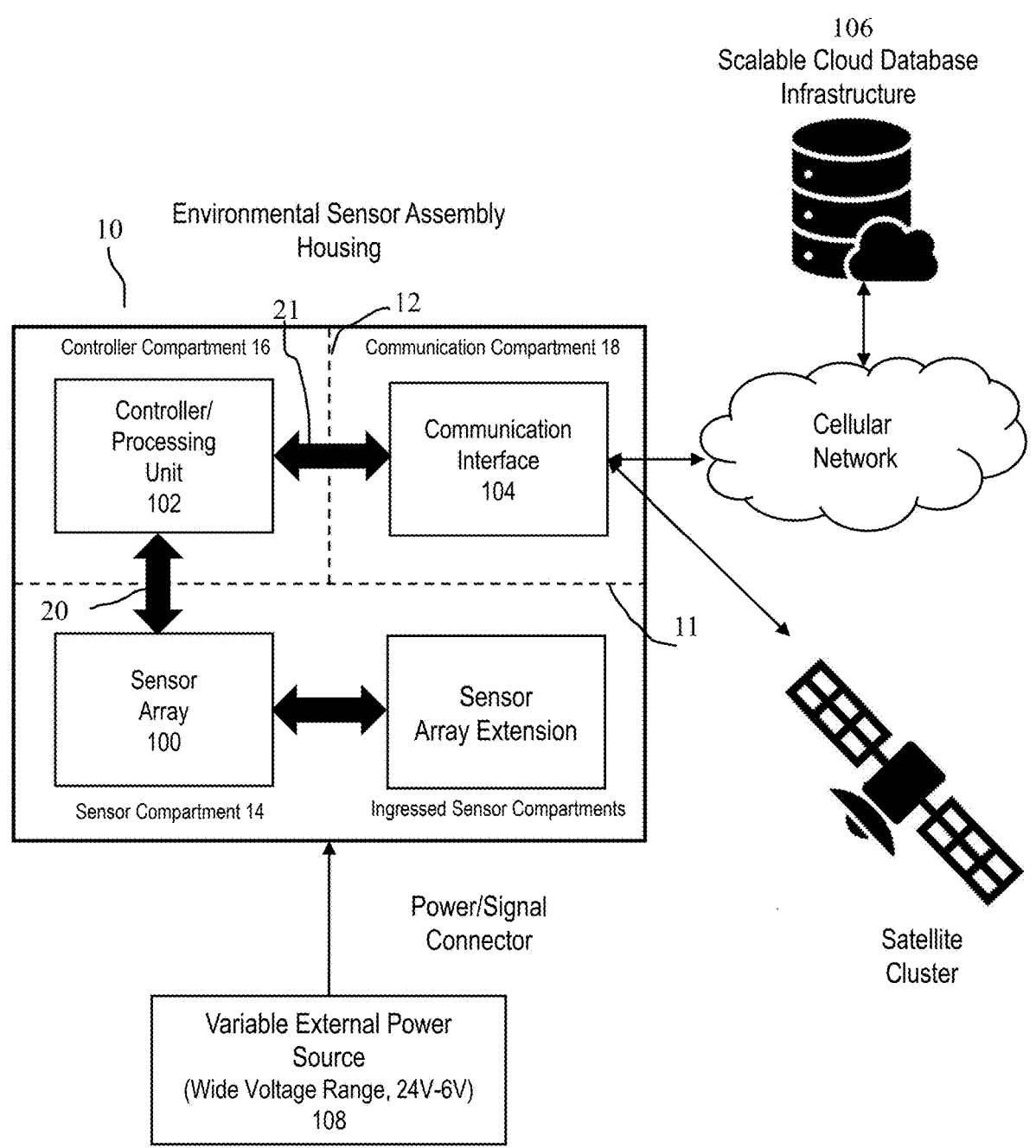
FIG. 1 shows a schematic representation of one embodiment of a sensor assembly.
Figure 3:
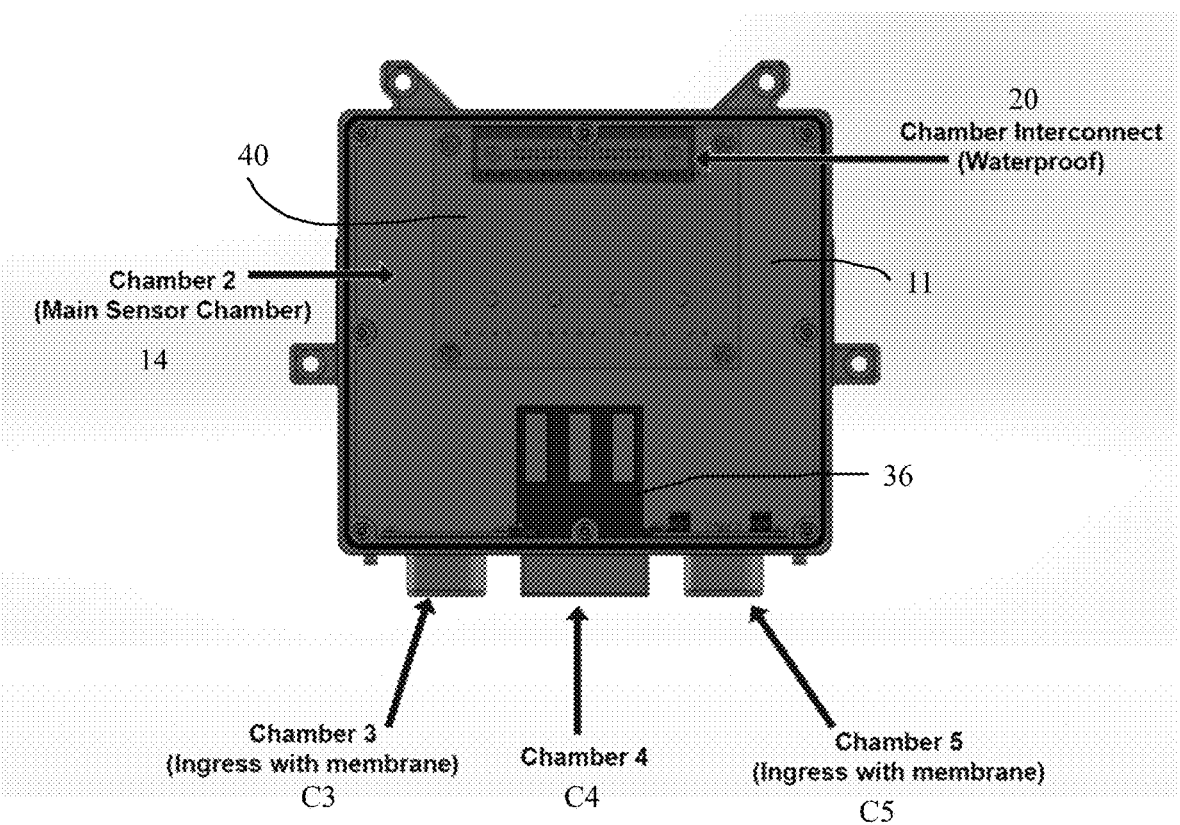
FIG. 3 is a plan view of a sensor compartment of the embodiment of FIG. 2.

The sensor assembly disclosed herein is intended to be used to monitor environmental conditions in different locations, in either a stationary installation or a mobile installation, such as when mounted to a vehicle or an aircraft such as a drone.

As used herein, an "environmental condition" refers to any physically measurable property of air and which can be measured by a sensor. Exemplary environmental conditions include a concentration of a gaseous component of air, such as carbon monoxide (CO), carbon dioxide ($CO_2$), nitrous oxide (NO), nitrogen oxides of the formula $NO_x$ such as nitrogen dioxide ($NO_2$), ozone ($O_3$), methane ($CH_4$), and sulfur oxides of the form $SO_x$ such as sulfur dioxide ($SO_2$). In other embodiments, the environmental condition may be a concentration of suspended particulate matter in general, or a concentration of suspended particulate matter of a specific composition such as lead. In still other non-limiting embodiments, the environmental condition may be a weather condition, such as air temperature, humidity, barometric pressure, and wind speed.

"GPS module" refers to a device that includes an antenna for receiving satellite navigation signals (e.g., signals transmitted by the Global Positioning System (GPS), the Global Navigation Satellite System (GLONASS), the Galileo positioning system, the Beidou Navigation Satellite System, or satellite navigation systems), and an operatively connected processor that is configured with a set of instructions stored on a memory, to analyze such signals to determine the location of the module, and optionally, other kinematic information such as distance travelled, direction of movement, speed, and acceleration of the module. GPS modules are known in the art, and do not, by themselves constitute the present invention. Persons skilled in the art may refer to a satellite navigation signal receiver module as a "GPS receiver," or a "GNSS receiver," depending on the type of satellite navigation signal used by the module.

"Memory" refers to a non-transitory tangible computer-readable medium for storing information in a format readable by a processor, and/or instructions readable by a processor to implement an algorithm. The term "memory" includes a plurality of physically discrete, operatively connected devices despite use of the term in the singular. Non-limiting types of memory include solid-state, optical, and magnetic computer readable media. Memory may be non-volatile or volatile. Instructions stored by a memory may be based on a plurality of programming languages known in the art, with non-limiting examples including the C, C++, Python™, MATLAB™, and Java™ programming languages.

"Mobile platform" refers to any device including a sensor which is not in a fixed stationary geolocation. Mobile platforms may include any consumer or industrial means of transportation, such as automobiles, trucks, buses, trains, tractors, motorcycles, or bicycles, whether powered or not. Mobile platforms may further include handheld or portable devices which are manually moved, such as by a pedestrian.

"Processor" refers to one or more electronic devices that is/are capable of reading and executing instructions stored on a memory to perform operations on data, which may be stored on a memory or provided in a data signal. The term "processor" includes a plurality of physically discrete, operatively connected devices despite use of the term in the singular. Non-limiting examples of processors include devices referred to as microprocessors, microcontrollers, central processing units (CPU), and digital signal processors.

"Plug-and-play" means that a component may be connected to the system and be operable without customization or configuration, other than with processes or algorithms to recognize the component and establish a communication path with the component.

In this description, the directional prepositions of up, upwardly, down, downwardly, front, back, top, upper, bottom, lower, left, right and other such terms refer to the device as it is oriented and appears in the drawings and are used for convenience only; they are not intended to be limiting or to imply that the device has to be used or positioned in any particular orientation. Conventional components of the invention are elements that are well-known in the prior art and will not be discussed in detail for this disclosure.

In some embodiments, the sensor assembly comprises a compartmentalized housing 10 which contains all the components necessary to create data comprising a sensor reading of at least one environmental condition, and communicate the data to another location. Thus, a sensor array 100 collects and provides data, which is processed by a controller/processor 102. The data may be stored temporarily or permanently to a memory, which may include removable physical memory devices. The data may then be transmitted by a communications interface 104 to a server 106, using a cellular network, WiFi, Bluetooth™, or another mode of wireless communication. In some examples, such as in stationary installations, the communications interface 104 may comprise a wired communication such as Ethernet or a USB cable. The system may also comprise a GPS module which allows location data to be collected and correlated to the sensor data, prior to transmission to server 106.

The sensor assembly provides a compact and lightweight assembly which can be mounted and used in a large variety of settings, including mobile platforms. This assembly permits a large number of sensors to be implemented in a relatively small footprint. For example, in one embodiment, the housing 10 is a rectangular box having external dimensions of about 18×7×16 cm, with an internal volume of about 2000 ml, of which about 40-60% may be allocated to a sensor compartment. The modular nature of the sensor fittings may permit a large number of sensors to be mounted in the assembly, for example up to about 20 different sensors may be mounted. Thus, a sensor density of 10 to 20 sensors per liter of volume of the sensor compartment may be achieved. The sensors may comprise any sensor which physically fits within the compartment and which is connectable to the electronics. Many commercially available sensors are suitable for installation and use.

The housing 10 comprises at least one divider 11 which separates a sensor compartment 14 from one or more systems compartments. The divider 11 may be vertical and parallel with the major surfaces of the housing. Preferably, the one or more systems compartments comprises a controller compartment 16 and a communications compartment 18, separated by a second divider 12. The second divider 12 is preferably horizontal and parallel with the minor surfaces of the housing. The housing 10 and dividers 11, 12 are conveniently manufactured from a suitable polymer or plastic material, such as by injection molding or additive manufacturing. As used herein, a "divider" is a physical barrier which is substantially impermeable to air and moisture. The dividers 11, 12 create sealed and separate compartments within the housing 10. FIGS. 2B and 2D show the compartments without components such as sensors, modems, or PCBs or other electronic components installed.

The compartments are closed with a front cover 24, and two rear covers 26, 28 and each cover is sealed with a gasket 30. The front cover 24 has a main opening (not shown) which is covered by a hood 32. Thus, the housing 10 is sealed to protect internal components from ambient conditions, except for at least one opening which allows air to circulate through the sensor compartment. Air openings to the sensor compartment may be completely open to the atmosphere, or may be covered with an air-permeable filter or membrane. Air circulation may be passive or active with small fans (not shown) to move air through as desired.

An interconnect 20 which passes through divider 11 is provided to provide effective signal communication from the sensor compartment 14 to the controller compartment 16, without the need for cables or wires to cross the dividers or run external to the housing 10. The interconnect 20 permits components in the sensor compartment to electronically communicate with the processor/controller in the controller compartment, but without creating any openings in the divider 11. The communications may be bi-directional, where control signals are sent to the sensors and sensor data is communicated back to the controller. A second interconnect 21 passes through or around divider 12 and provides connections between the controller compartment and the communications compartment. The interconnects 20, 21 may comprise an electrical interconnect having one or more pin and socket type connectors.

Electrical connections within each compartment, from one component to another and/or to distribute power, may be made with conventional flat ribbon cable 23, with suitable connectors.

In a preferred embodiment, the sensor compartment 14 may comprise one or more smaller subchambers for specific sensors or groups of sensors. The subchambers may comprise small cylindrical or rectangular enclosures which house the sensor, but which is connected to and disposed within the main sensor compartment. For example, as shown in the Figures, a first subchamber (C4) may be configured to fit a particular sensor with passive, unfiltered airflow which has been quieted by baffle 36. This may be suitable for installation of a particulate matter sensor, for example. Second and third subchambers (C3 and C5) may be provided with membrane-filtered airflows, optionally with small fans (not shown) drawing air in past the sensor. Subchambers C3 and C5 also have quieted airflow due to the reduction in air velocity and turbulence.

The plurality of sensors may include commercially available MEMS, electromechanical, optical or ultrasonic sensors. For example, the plurality of sensors may be selected from the group consisting of sensors specific to certain gases (ammonia, methane, sulfur dioxide, nitric oxide, hydrogen sulfide, carbon dioxide, carbon monoxide, indoor air quality (IAQ), ozone, ethanol, volatile organic compounds such as isobutylene or toluene), temperature sensor, temperature sensor, humidity sensor, air pressure sensor, wind sensor, or particulate matter sensor.

A plurality of sensor plugins 34 may be provided within the sensor compartment, each to receive or connect to a particular sensor in a "plug-and-play" manner. The sensor plugins may comprise connectors for implementing specific communication protocols, such as RS485, UART, I2C, SPI and/or Canbus protocols. Each sensor plugin will be operatively connected, for example with flat ribbon cables, to a PCB board 40 or the interconnect 20 to communicate signals to the controller compartment. A large number of sensor plugins 34 may be provided on a single PCB board 40 to install sensors 42, as exemplified in FIG. 4.

Figures 4, 5A, 5B:
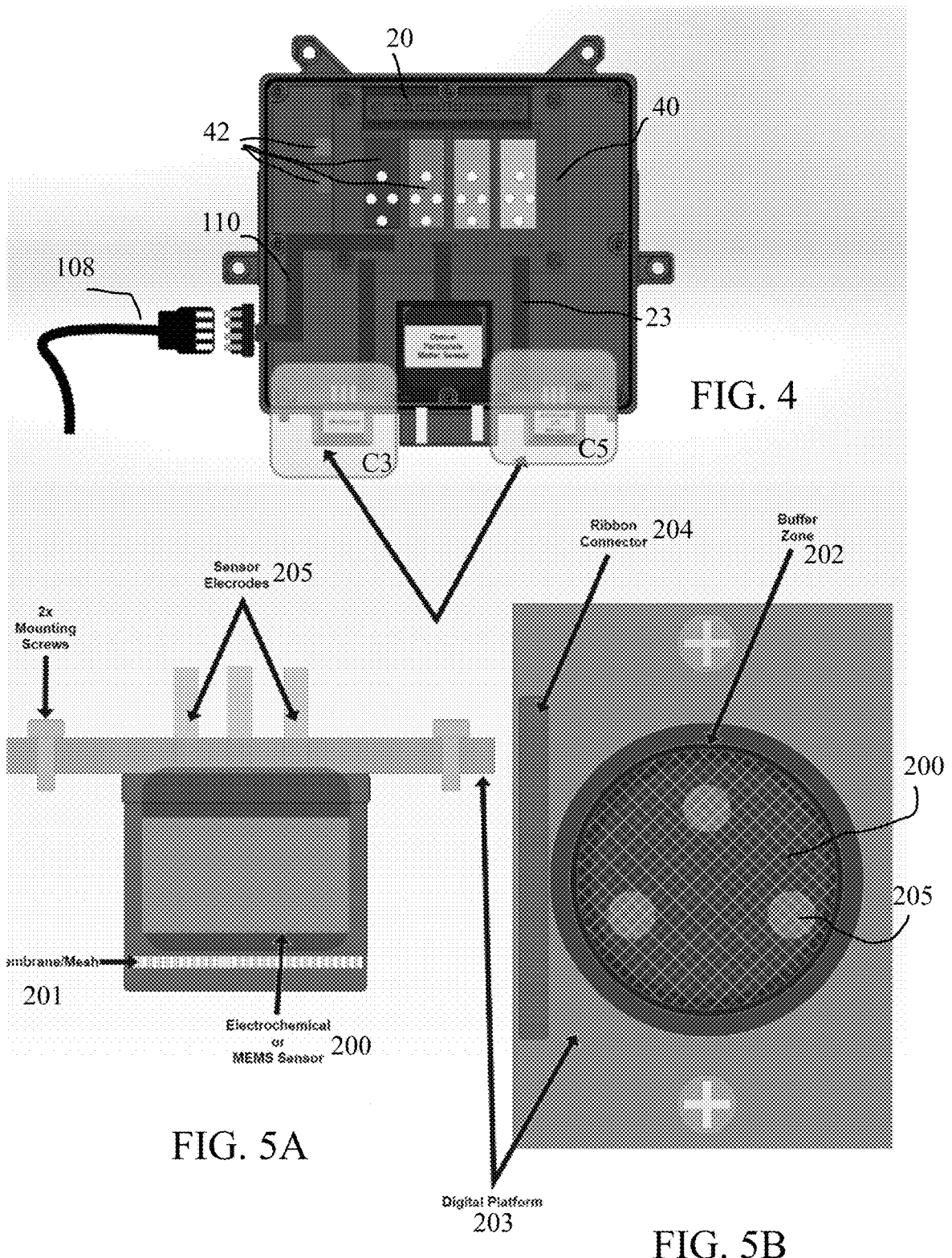
FIG. 4 is a view of the sensor compartment with a plurality of sensors installed.
FIG. 5A is a vertical cross-sectional view of a sensor subchamber shown in FIG. 4.
FIG. 5B is a top plan view of the same sensor subchamber.

One exemplary sensor installation is shown in FIGS. 5A and 5B, where an electrochemical or MEM sensor 200 is installed in a sensor subchamber C3 which has an air inlet with a membrane, mesh or screen 201 positioned across the inlet. Airflow may pass around the sensor in a buffer zone 202. The sensor is mounted to a digital platform 203 physically mounted to the housing and electrically connected with a ribbon connector 204. Sensing electrodes 205 may protrude into the sensor compartment space. The controller/processor 102 implements algorithms to control the sensors, collect desired data, and to communicate with server 106. The controller/processor 102 may comprise any computer processor and may be installed as a PCB.

The sensor assembly comprises a power distribution subsystem 110 which is configured to receive power from an external power source 108, operating within a wide voltage range, such as 4V to 24V. Different components and digital sensors may require different voltages. Power is provided, as needed, to components within each of the compartments through the electrical interconnects.

In preferred embodiments, the airflow through the sensor compartment may be regulated to avoid temperature extremes to accommodate sensors that may have temperature-dependent properties or operation limits. In some embodiments, a small heating element may be provided, such as an electric resistive heater (not shown) . . . . One or more fans and/or heat sinks may be provided, particularly in connection with the controller/processor or communication interface components to dissipate heat in the assembly.

In preferred embodiments, the rear cover includes mounting bracket fittings 36 which attach to a variety of different mounting brackets, for stationary or mobile installations. Interpretation.

The corresponding structures, materials, acts, and equivalents of all means or steps plus function elements in the claims appended to this specification are intended to include any structure, material, or act for performing the function in combination with other claimed elements as specifically claimed.

References in the specification to "one embodiment", "an embodiment", etc., indicate that the embodiment described may include a particular aspect, feature, structure, or characteristic, but not every embodiment necessarily includes that aspect, feature, structure, or characteristic. Moreover, such phrases may, but do not necessarily, refer to the same embodiment referred to in other portions of the specification. Further, when a particular aspect, feature, structure, or characteristic is described in connection with an embodiment, it is within the knowledge of one skilled in the art to affect or connect such module, aspect, feature, structure, or characteristic with other embodiments, whether or not explicitly described. In other words, any module, element or feature may be combined with any other element or feature in different embodiments, unless there is an obvious or inherent incompatibility, or it is specifically excluded.

It is further noted that the claims may be drafted to exclude any optional element. As such, this statement is intended to serve as antecedent basis for the use of exclusive terminology, such as "solely," "only," and the like, in connection with the recitation of claim elements or use of a "negative" limitation. The terms "preferably," "preferred," "prefer," "optionally," "may," and similar terms are used to indicate that an item, condition or step being referred to is an optional (not required) feature of the invention.

The singular forms "a," "an," and "the" include the plural reference unless the context clearly dictates otherwise. The term "and/or" means any one of the items, any combination of the items, or all of the items with which this term is associated. The phrase "one or more" is readily understood by one of skill in the art, particularly when read in context of its usage.

The term "about" can refer to a variation of +5%, +10%, +20%, or +25% of the value specified. For example, "about 50" percent can in some embodiments carry a variation from 45 to 55 percent. For integer ranges, the term "about" can include one or two integers greater than and/or less than a recited integer at each end of the range. Unless indicated otherwise herein, the term "about" is intended to include values and ranges proximate to the recited range that are equivalent in terms of the functionality of the composition, or the embodiment.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. A recited range includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc.

As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio.

The invention claimed is:

1. An environmental sensor assembly comprising:
a. a housing having at least one internal divider defining a sensor compartment and at least one system compartment, wherein the sensor compartment defines at least one opening to provide gas communication to the atmosphere;
b. an interconnect providing electrical connections between the sensor compartment and a systems compartment; and
c. a plurality of sensors each mounted in the sensor compartment in a detachable manner and operably connected to the interconnect;
d. wherein the sensor compartment and the at least one system compartment are sealed and separate, and e. wherein the at least one system compartment is divided into a controller compartment comprising a controller and a communications compartment comprising at least one communications interface, wherein the controller compartment and the communications compartment are sealed and separate, with an interconnect providing electrical connections between the two.

2. The assembly of claim 1, wherein the sensor compartment comprises a plurality of sensor plugins each comprising a plug-and-play connector for operatively connecting a sensor.

3. The assembly of claim 1, wherein the sensor compartment comprises at least one subchamber partially defined by an air-permeable element.

4. The assembly of claim 3 wherein the air-permeable element is a baffle, screen or membrane.

5. The assembly of claim 1 further comprising a temperature-regulating element.

6. The assembly of claim 5 wherein the temperature-regulating element is a heater, a fan or a heat-sink.

7. The assembly of claim 1, wherein the assembly has a sensor density of between 10 to 20 sensors per liter of sensor compartment volume.

8. The assembly of claim 1, wherein the communications interface is adapted to transmit data using at least one of a cellular network, a WiFi network, or a Bluetooth connection.

* * * * *